(12) United States Patent
Marin Palacios et al.

(10) Patent No.: US 7,898,251 B2
(45) Date of Patent: Mar. 1, 2011

(54) METHOD AND SYSTEM FOR THE INDIVIDUALIZED CHARACTERIZATION OF MAGNETIC ELEMENTS BASED ON FERROMAGNETIC RESONANCE

(75) Inventors: Pilar Marin Palacios, Pozuelo De Alarcon (ES); Daniel Cortina Blanco, Boadilla Del Monte (ES); Javier Calvo Robledo, Pozuelo De Alarcon (ES); Antonio Hernando Grande, Madrid (ES)

(73) Assignee: Micromag 2000, S.L., Madrid (ES)

( * ) Notice: Subject to any disclaimer, the term of this patent is extended or adjusted under 35 U.S.C. 154(b) by 399 days.

(21) Appl. No.: 11/705,723

(22) Filed: Feb. 14, 2007

(65) Prior Publication Data

US 2007/0187513 A1 Aug. 16, 2007

(30) Foreign Application Priority Data

Feb. 14, 2006 (ES) ................................ 200600336

(51) Int. Cl.
*G01V 3/00* (2006.01)

(52) U.S. Cl. ........................ 324/300; 324/307; 324/318; 324/301

(58) Field of Classification Search ......... 324/300–322, 324/244; 174/36, 110 R, 122 G, 94 R, 394; 235/435; 340/572.5; 342/1; 600/410, 411, 600/422; 315/5.22; 361/146

See application file for complete search history.

(56) References Cited

U.S. PATENT DOCUMENTS 2,750,531 A * 6/1956 Sterling ..................... 315/5.22
2,975,360 A * 3/1961 Bell ............................ 324/244

(Continued)

FOREIGN PATENT DOCUMENTS

WO 96/05522 2/1996

(Continued)

OTHER PUBLICATIONS

Marín, P. et al., "*Applications of Amorphous and Nanocrystalline Magnetic Materials*" Journal of Magnetism and Magnetic Materials, 215-216 (2000) pp. 729-734.

(Continued)

*Primary Examiner*—Melissa J Koval
*Assistant Examiner*—Tiffany A Fetzner
(74) *Attorney, Agent, or Firm*—Wenderoth, Lind & Ponack, L.L.P.

(57) ABSTRACT

A method and system for the characterization of a magnetic element based on ferromagnetic resonance, the magnetic element presents ferromagnetic resonance and its own characteristic resonance frequency. The system includes mechanism for application of a low-frequency electromagnetic field in a given area; a mechanism for application of a high-frequency electromagnetic wave the same as the characteristic resonance frequency of the magnetic element in the same area; and a control unit configured so as to control the simultaneous application of the low-frequency electromagnetic field so that in response to the introduction of the magnetic element in the area the magnetic element absorbs the high-frequency electromagnetic wave with a frequency the same as that of the low-frequency electromagnetic field, so the wave is modulated. The system also comprises a mechanism for reception of this unique individual modulated wave characteristic of each element, and a mechanism for assignment of the unique modulated wave to the element.

9 Claims, 5 Drawing Sheets

U.S. PATENT DOCUMENTS

| | | | | |
|---|---|---|---|---|
| 2,982,909 | A * | 5/1961 | Melchor et al. | 324/300 |
| 3,174,098 | A * | 3/1965 | Shapiro | 324/310 |
| 3,405,326 | A * | 10/1968 | Barton, Jr. et al. | 361/146 |
| 5,484,992 | A | 1/1996 | Wilz et al. | 235/462.08 |
| 6,227,450 | B1 | 5/2001 | Blake et al. | 235/462.36 |
| 6,232,879 | B1 | 5/2001 | Tyrén | 340/572.6 |
| 6,765,144 | B1 * | 7/2004 | Wang et al. | 174/36 |
| 7,041,911 | B2 * | 5/2006 | Marin Palacios et al. | 174/110 R |
| 7,128,988 | B2 * | 10/2006 | Lambeth | 428/831.2 |
| 7,202,667 | B2 * | 4/2007 | Barbic | 324/318 |
| 7,336,215 | B2 * | 2/2008 | Marin Palacios et al. | 342/1 |
| 7,473,843 | B2 * | 1/2009 | Wang et al. | 174/36 |
| 2003/0136837 | A1* | 7/2003 | Amon et al. | 235/435 |
| 2004/0058196 | A1* | 3/2004 | Lambeth | 428/694 BH |
| 2005/0025797 | A1* | 2/2005 | Wang et al. | 424/422 |
| 2005/0077073 | A1* | 4/2005 | Marin Palacios et al. | 174/94 R |
| 2005/0079132 | A1* | 4/2005 | Wang et al. | 424/1.11 |
| 2005/0107870 | A1* | 5/2005 | Wang et al. | 623/1.44 |
| 2005/0149002 | A1* | 7/2005 | Wang et al. | 606/1 |
| 2005/0149169 | A1* | 7/2005 | Wang et al. | 623/1.15 |
| 2005/0236486 | A1 | 10/2005 | Blake et al. | 235/462.37 |
| 2006/0001423 | A1* | 1/2006 | Barbic | 324/300 |
| 2006/0118319 | A1* | 6/2006 | Wang et al. | 174/36 |
| 2006/0142853 | A1* | 6/2006 | Wang et al. | 623/1.46 |
| 2006/0170583 | A1* | 8/2006 | Marin Palacios et al. | 342/1 |
| 2006/0255799 | A1* | 11/2006 | Reiderman | 324/303 |
| 2007/0010702 | A1* | 1/2007 | Wang et al. | 600/8 |
| 2007/0187513 | A1* | 8/2007 | Marin Palacios et al. | 235/462.37 |
| 2007/0194927 | A1* | 8/2007 | Peter et al. | 340/572.5 |
| 2008/0084307 | A1* | 4/2008 | Peter et al. | 340/572.1 |
| 2008/0131545 | A1* | 6/2008 | Peter et al. | 425/142 |
| 2008/0143533 | A1* | 6/2008 | Marin Palacios et al. | 340/572.5 |
| 2009/0145239 | A1* | 6/2009 | Girshovich et al. | 73/779 |

FOREIGN PATENT DOCUMENTS

WO  00/75895  12/2000

OTHER PUBLICATIONS

Marín, P. et al., "*High-Frequency Behavior of Amorphous Microwires and its Applications*" Journal of Magnetism and Magnetic Materials, 290-291 (2005) pp. 1597-1600.

Herzer, G. et al., "*Round Table Discussion: Present and Future Applications of Nanocrystalline Magnetic Materials*" Journal of Magnetism and Magnetic Materials, 294 (2005) pp. 252-266.

\* cited by examiner

METHOD AND SYSTEM FOR THE INDIVIDUALIZED CHARACTERIZATION OF MAGNETIC ELEMENTS BASED ON FERROMAGNETIC RESONANCE

FIELD OF THE INVENTION

The present invention refers to a method and a system for characterizing magnetic, preferably amorphous elements individually based on the ferromagnetic resonance phenomenon.

The invention lies within the technical field of magnetic materials, covering also aspects of electromagnetism, with application in the field of sensors, detectors and encoders.

BACKGROUND OF THE INVENTION

The encoding of objects is a field of great interest from the point of view of their classification and identification. The most widespread methods of encoding are bar codes, radiofrequency circuits (RFID) and magnetic materials. In each of these methods the codes have the corresponding reader associated.

Bar codes are read by passing a small point of laser light over the printed bar code symbol. The darks bars absorb the light source from the scanner and this is reflected in the luminous spaces. The function of the scanner is to read the bar code symbol and provide the computer with an electrical output corresponding to the bars and spaces of the bar code. It is the decoder, however, that recognizes the bar code symbols, analyzes the content of the read bar code and transmits these data to the computer in a traditional data format. Examples of this technology may be found in United States patent application US-A1-2005/236486 or in the U.S. Pat. No. 6,227,450 or U.S. Pat. No. 5,484,992.

As their active element, radiofrequency labels have an LC circuit (inductance-condenser) and are activated by means of an electromagnetic wave whose frequency coincides with the resonance frequency of the circuit. A receiving antenna detects the presence of the circuit activated. In the case of the simplest labels encoding is done by varying the circuit impedance: in the more complex cases the LC circuit is connected to a chip containing information.

Conventional magnetic labels have the information on a magnetic carrier. Until now labels of this type have been activated by an alternating magnetic field and their detection carried out by electromagnetic induction.

A soft magnetic material is characterized in that it is magnetized in the presence of an alternating magnetic field and it is demagnetized constantly according to the direction of the field applied. The hysteresis loop of each material gives account of this behavior.

Amorphous magnetic materials exhibit optimum properties as soft magnetic elements and, in particular, they have a property known as ferromagnetic resonance. In particular, magnetic wires and microwires have an easy magnetization axis in their longitudinal direction. When a low-frequency magnetic field is applied, its magnetization is oriented in this longitudinal direction and precesses with a frequency of its own around the easy axis.

SUMMARY OF THE INVENTION

The invention refers to a method and a system for the individualized characterization of magnetic elements based on ferromagnetic resonance according to claim 1 and claim 9, respectively. Preferred embodiments of the method and the system are defined in the dependent claims.

In accordance with an initial aspect of the present invention, this refers to a method for the characterization of a magnetic element based on ferromagnetic resonance in which the magnetic element presents the property of ferromagnetic resonance and a resonance frequency of its own, the method comprising the following steps:

application of a low frequency electromagnetic field in a given area.

application at the same time in the same area of an electromagnetic wave of a high frequency the same as the characteristic resonance frequency of a magnetic element.

introduction of the magnetic element into the given area, with the result that this absorbs the high-frequency electromagnetic wave with a frequency the same as that of the low-frequency electromagnetic field, so that the wave is modulated; the method also comprises:

reception of this unique individual modulated wave characteristic of each magnetic element, and assignment of said unique modulated wave to the magnetic element.

Assigning the unique individual modulated wave characteristic of each magnetic element to the magnetic element may include encoding (by means of some known encoding technique) the modulated wave.

Preferably each magnetic element is characterized by a low-frequency hysteresis loop; the hysteresis loop and the characteristic resonance frequency are determined by the composition and geometry of the magnetic element.

The magnetic element is preferably an amorphous magnetic element; it may be a magnetic microwire.

The frequency of the low-frequency electromagnetic field is preferably between 50-800 Hz.

The frequency of the high-frequency electromagnetic wave is preferably between 0.5-20 GHz.

In accordance with a second aspect of the present invention, this refers to a system for the characterization of a magnetic element based on ferromagnetic resonance, said magnetic element presenting the property of ferromagnetic resonance and a characteristic resonance frequency of its own; the system comprises:

means of application of a low-frequency electromagnetic field in a given area.

means of application of a high-frequency electromagnetic wave the same as the characteristic resonance frequency of the magnetic element in that same given area.

control means configured so as to control the simultaneous application of the low-frequency electromagnetic field and the high-frequency electromagnetic wave, with the result that in response to the introduction of the magnetic element in the given area, the magnetic element absorbs the high-frequency electromagnetic wave with a frequency the same as that of the low-frequency electromagnetic field, so the wave is modulated; the system also comprises:

means of reception of the unique individual modulated wave characteristic of each magnetic element, and means of assignment of said unique modulated wave to the magnetic element.

The means of assignment of the unique individual modulated wave characteristic of each magnetic element to the magnetic element preferably include means of encoding the modulated wave.

Each magnetic element is preferably characterized by a low-frequency hysteresis loop and its own resonance frequency; the hysteresis loop and the characteristic resonance frequency are determined by the composition and geometry of the magnetic element.

The magnetic element is preferably an amorphous magnetic element; it can be a magnetic microwire.

The frequency of the low-frequency electromagnetic field is preferably between 50-800 Hz.

The frequency of the high-frequency electromagnetic wave is preferably between 0.5-20 GHz.

As stated above, the magnetic elements (wires, microwires or magnetic strips) possess an easy magnetization axis in their longitudinal direction; when a low-frequency magnetic field is applied, the magnetization of such a magnetic element is oriented in this longitudinal direction, and precesses with a frequency of its own (the characteristic resonance frequency) around the easy axis.

By means of the method and system of the present invention a low-frequency field is applied to the magnetic element coinciding with the incidence of a high-frequency electromagnetic wave the same as the magnetic element magnetization precession wave. The ferromagnetic resonance phenomenon gives rise to a high imaginary part of the magnetic permeability for high frequencies (normally comprised between 0.5-20 GHz), so the magnetic element is capable of absorbing the electromagnetic wave with a frequency that is the frequency of the low-frequency magnetic field being applied; in this way, the high-frequency electromagnetic wave is modulated by said low frequency.

In other words, the method for individualized characterization of magnetic elements is based on the modulation undergone by a high-frequency electromagnetic wave in the presence of the magnetic element when this is in the presence of a low-frequency magnetic field.

This modulation has the same period as the low-frequency field applied and has its origin in the ferromagnetic resonance experienced by the magnetic element.

The invention also refers to the use of a method of individualized characterization of a magnetic element as explained above for identifying said magnetic element, which comprises:

carrying out an initial characterization on a first magnetic element, thereby obtaining a first unique modulated signal by applying the method of characterization defined above applying the method of characterization defined above to a second single modulated wave comparing said first and second modulated waves and, if they are the same, identifying the second magnetic element as said first magnetic element.

BRIEF DESCRIPTION OF THE DRAWINGS

The following series of drawings will assist in a clearer appreciation of the invention and which are expressly related to an embodiment of the invention, which is presented as a non-restrictive specimen of the same.

FIG. 4 is inserted into a device of the characteristics of that represented in FIG. 3.

DESCRIPTION OF A PREFERRED EMBODIMENT OF THE INVENTION

Figure 1A:
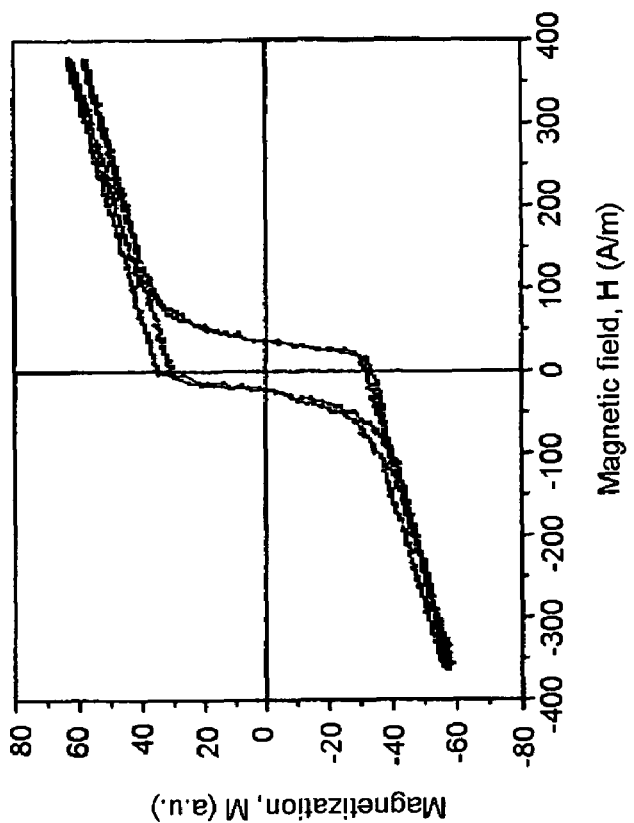
FIGS. 1A and 1B show the hysteresis loops corresponding to two different magnetic elements obtained at a frequency of 80 Hz.
Figure 1B:
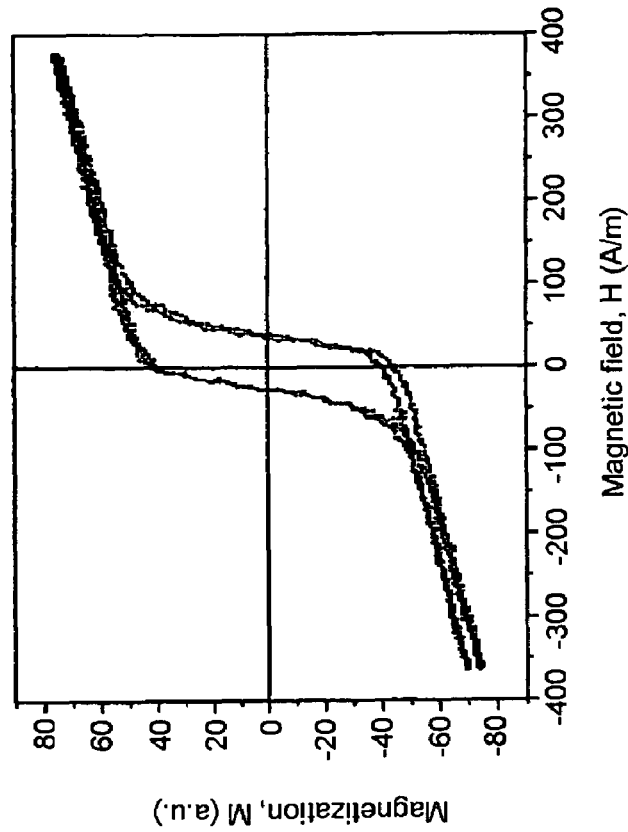

FIGS. 1A and 1B show hysteresis loops obtained for the different elements, applying in both cases an alternating magnetic field of 80 Hz and with a maximum value of 350 A/m. In this case it is a question of two amorphous magnetic microwires of FeCoSiBC composition.

Figure 2:
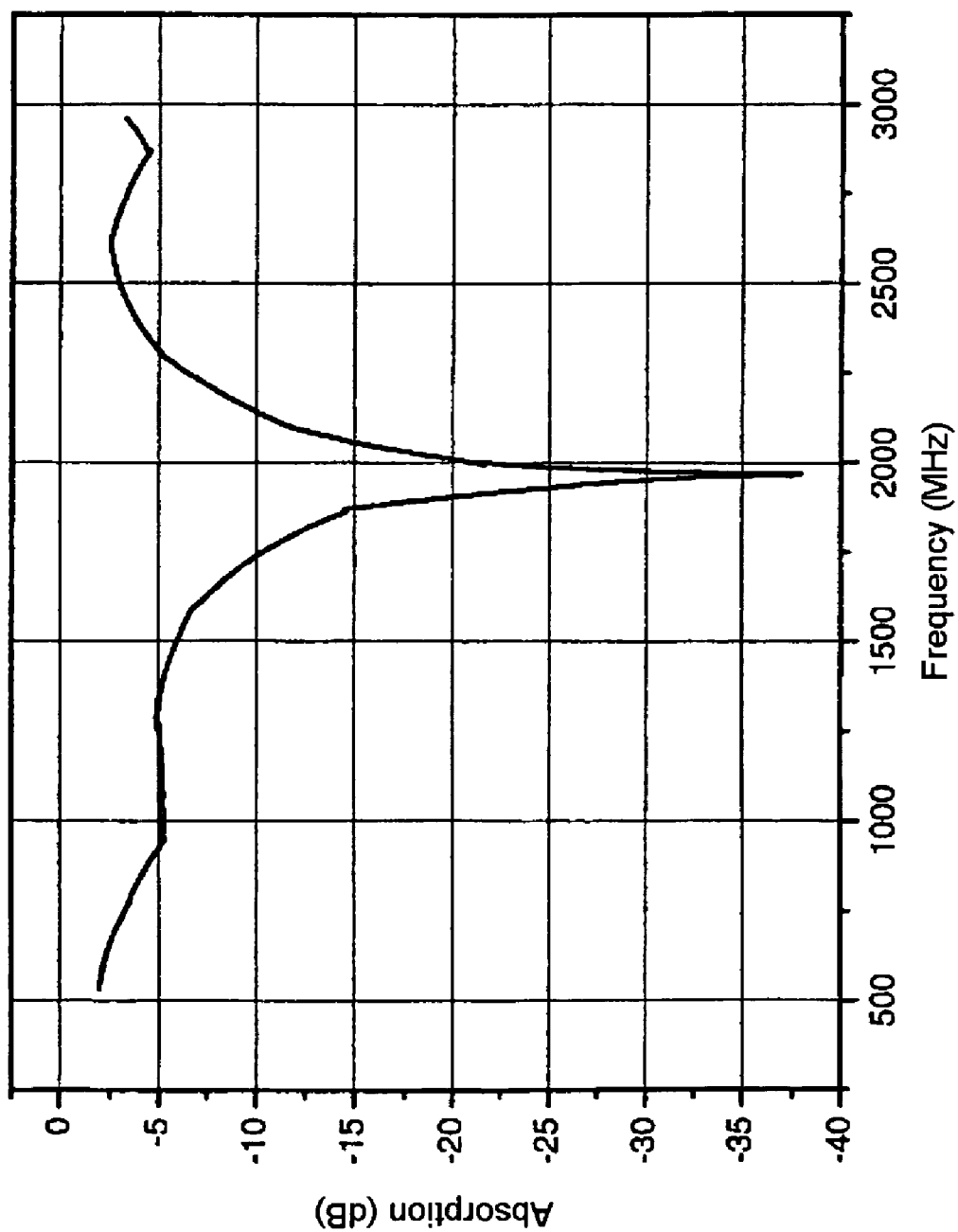
FIG. 2 shows the electromagnetic absorption spectrum corresponding to the magnetic elements whose hysteresis loop is shown in FIG. 1.

FIG. 2 shows the electromagnetic absorption spectrum corresponding to the microwires characterized in FIGS. 1A and 1B. From this it may be seen that samples of this type with a FeCoSiBC composition present the ferromagnetic resonance phenomenon for frequencies lying between 1.5-2.55 GHz.

Figure 3:
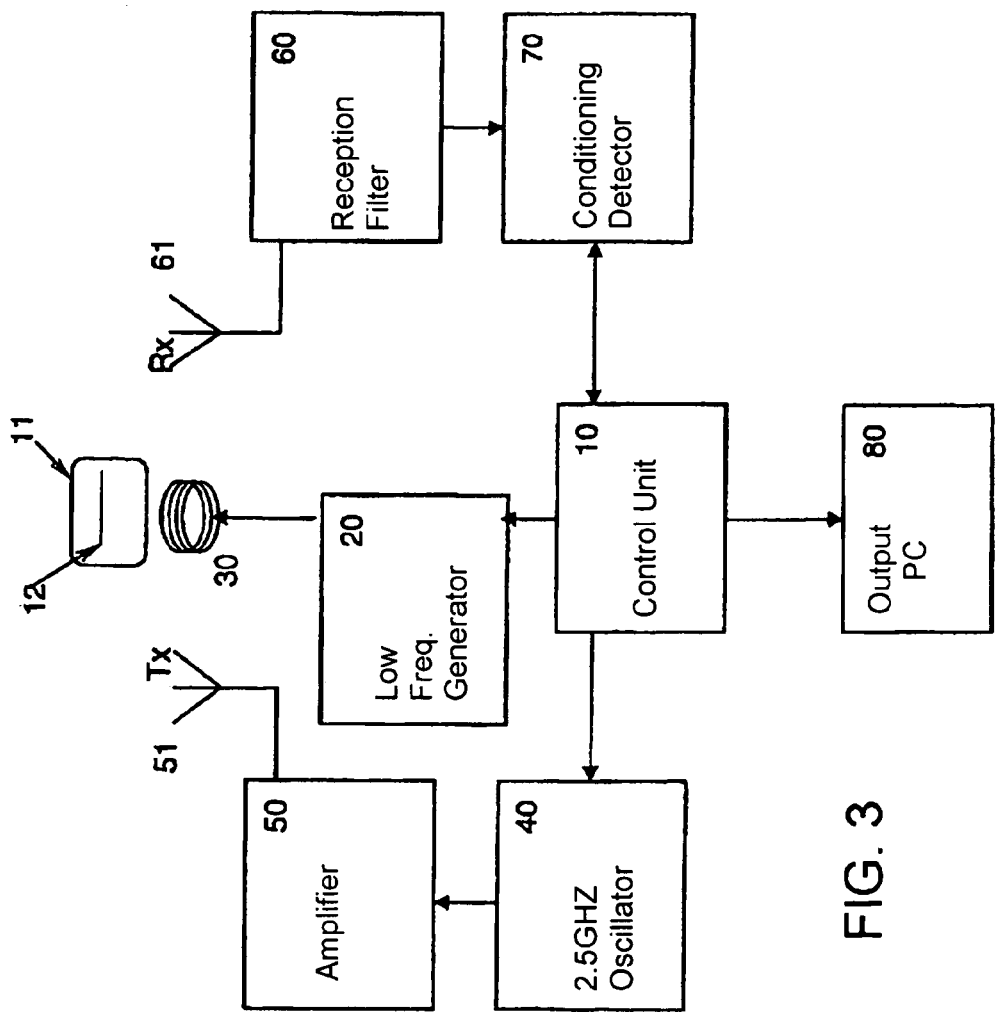
FIG. 3 shows a block diagram of the device to be used for the characterization of the amorphous magnetic element.

FIG. 3 shows the device used to characterize the magnetic element, which in this specific case is a card 11, which incorporates an amorphous magnetic wire 12. The device consists of a control unit 10, a low-frequency field generator 20 connected to a coil 30, a 2.5 GHz oscillator connected to an amplifier 50 and to a transmitting antenna 51. The device also includes a receiving antenna 61 connected to an amplifier and a reception filter 60 connected to a signal conditioning detector 70. The control unit has an output 80 connected for information which is sent to a PC. The device will also have the corresponding power supply (not illustrated).

Each card incorporates a magnetic microwire, which is characterized by its hysteresis loop, it is inserted in the characterization device described above (and shown in FIG. 3).

The characterization, unique for each magnetic element (amorphous magnetic microwire in this case), is carried out in the following way:

The low-frequency alternating field magnetizes and demagnetizes the sample specimen (amorphous microwire) constantly in accordance with its frequency, taking the specimen to maximum positive magnetization, decreasing it to zero and taking it back again to maximum but negative magnetization (this is a hysteresis loop). When the specimen is magnetized, either positively or negatively (saturated by the field), the magnetization starts to precess in the direction of the axis of the specimen (the microwire) with a frequency characteristic of the amorphous material, which may be from 0.5-20 GHz. However, when the alternating field passes through zero and the specimen is no longer magnetized, there is not such precision. The incidence of the high-frequency wave (0.5-20 GHz) is constant but it is only absorbed by the specimen when this is saturated, i.e. with maximum positive or negative magnetization. This whole process means that the receiving antenna 61 observes changes in the wave, which it receives in a periodic way; hence we say that it is modulated. The modulation is conditioned not only by the type of specimen which it sets out to detect (by way of its hysteresis loop, which is in turn determined by the composition and the geometry of the specimen), but also by the frequency of the low-frequency field. The modulated signal obtained by the receiving antenna is therefore unique and individual for each magnetic element.

The response of the microwire 12 subjected simultaneously to a low-frequency alternating magnetic field and to an electromagnetic wave of 2.5 GHz is detected by means of the receiving antenna 81 and passes by way of the respective filters to the control unit 10.

In other words, the modulated signal picked up at the receiving antenna (which is unique for each magnetic element), which is of the same frequency as that of the low-frequency field, is treated in such a way that a finite number of digits is associated univocally with each magnetic element, which means that one element can be distinguished from another.

Accordingly, a device that includes a transmitting antenna connected to a high-frequency generator, with a coil connected to a low-frequency current generator, and a receiving antenna connected to a signal conditioning detector enables the magnetic element to be identified.

Figure 4:
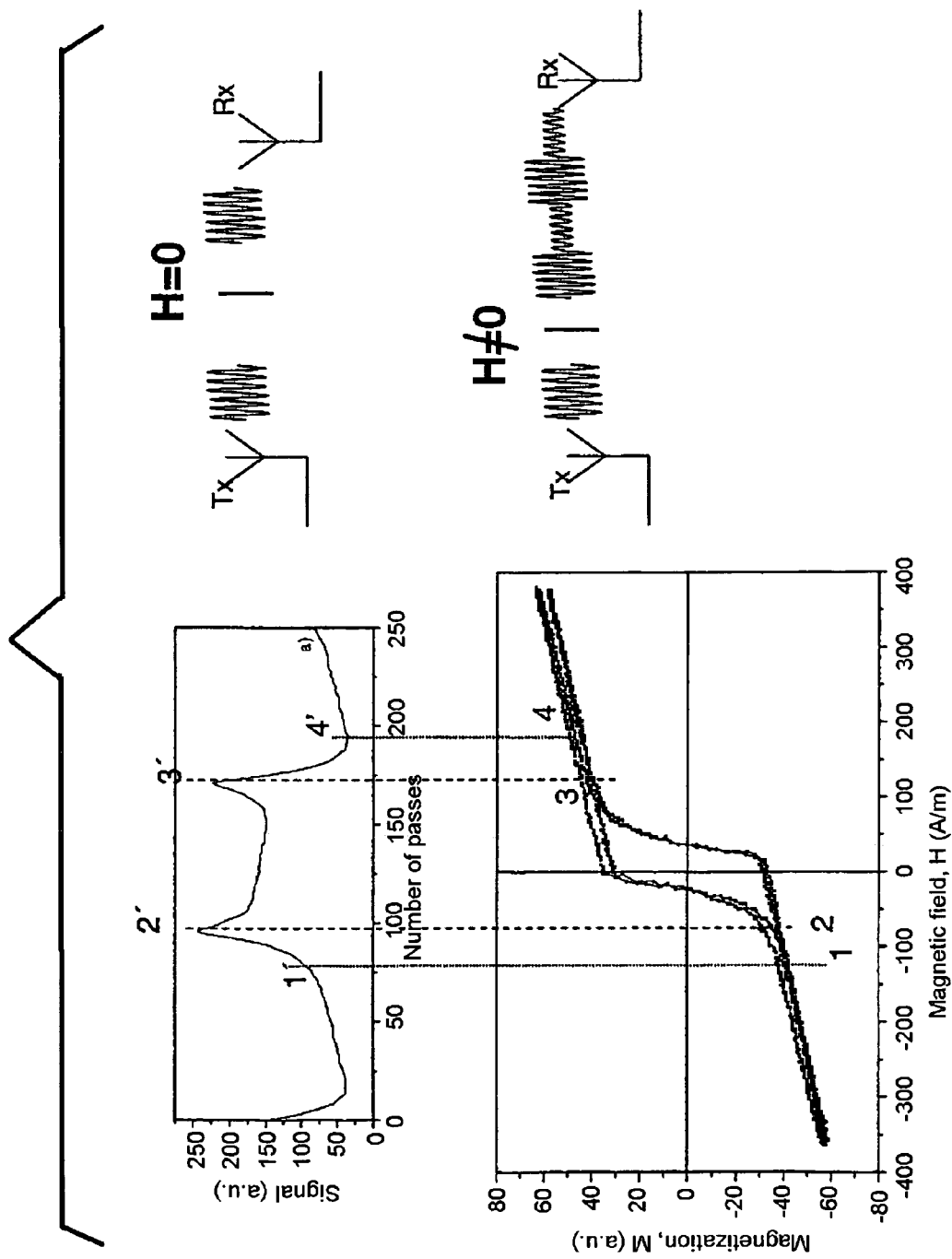
FIG. 4 shows the signal detected by the reception antenna when a magnetic element with a hysteresis loop as represented in the same

The upper part of FIG. 4 shows the signal detected by the receiving antenna 61 when a card with a magnetic microwire that has a hysteresis loop as represented also in FIG. 4 (lower part) is inserted in the characterization device of the present invention.

Figure 5A:
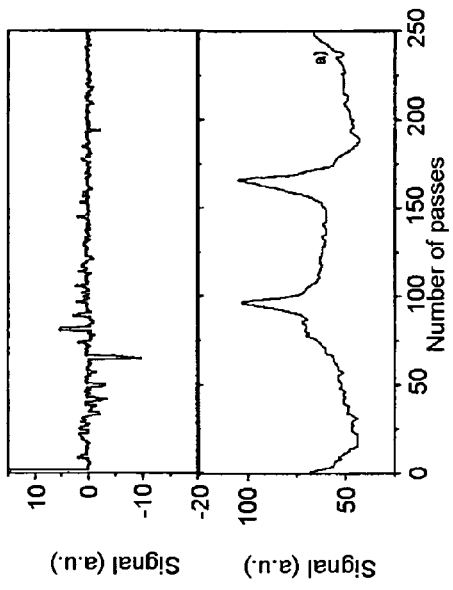
FIGS. 5A and 5B show the signals detected for the magnetic elements whose hysteresis loop is presented in FIG. 1; and for those same elements when a modification is effected in their placement in relation to the axis of the low-frequency field magnetizing coil, FIGS. 5C and 5D. All these graphs are accompanied by their respective transformations.
Figure 5C:
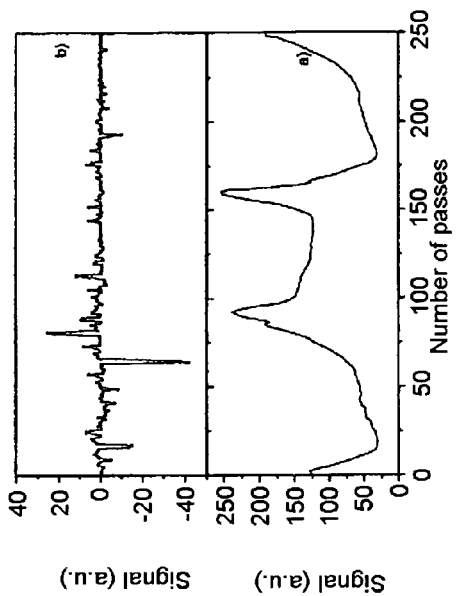
Figure 5B:
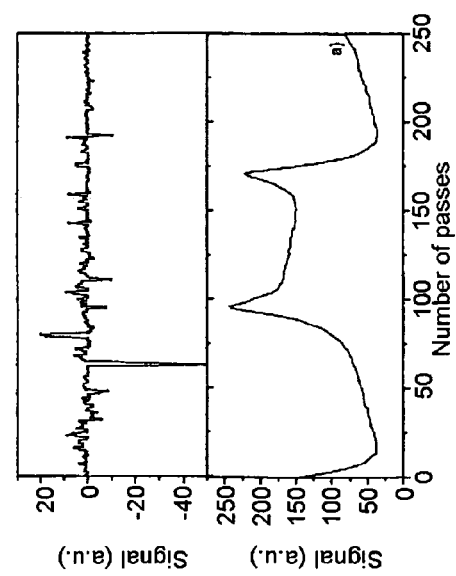
Figure 5D:
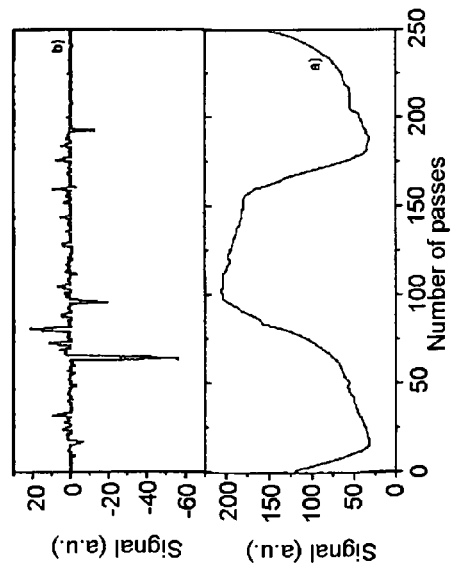

The signals detected by the receiving antenna for the two magnetic elements whose hysteresis loop is illustrated in the figure are shown in FIGS. 5a and 5b). If the microwire is turned in relation to the axis of the low-frequency field coil, a variation in the signal is observed, as shown in FIGS. 5c and 5d).

As stated, using a known technique the control unit executes the respective transformation of the signal by assigning a unique code to each microwire (FIG. 5b).

In this way, each magnetic microwire is characterized in an individualized manner by a unique code, which is determined by the composition and the geometry of the same as well as by the direction and frequency of the low-frequency electromagnetic field.

A possible application of the method and system of the invention could be as follows:

In this specific case the card is a credit or debit card 11' of the type used by banking or financial institutions. Conventionally, this card 11' has a magnetic strip on which the data associated with a single user or client of a banking institution are kept.

At the present time there is a technique for the falsification of such cards 11' consisting of copying the data from this magnetic strip onto another card (on another carrier), which may then be used "freely" by another unauthorized user.

This fraudulent use of cards may be prevented by means of the present invention in the following way:

Besides the respective unique magnetic strip, each card 11' incorporates a given sample specimen of amorphous magnetic microwires (being microwires, these may be "embedded" in the card without much difficulty).

This card 11' with the respective specimen of magnetic microwire is inserted into a characterization device like that of the present invention, by which it is characterized by means of the assignment of a unique coding (according to the modulated signal that reaches the receiving antenna of the device of the invention); in this way, the card 11' is assigned a unique magnetic strip and a unique coding.

Fraudulent use of this card is prevented if a device like that of the present invention is added to the conventional card 11' reader (for reading the magnetic strip of the card 11'). In this way, the use of said card is not permitted in the event of the data read from the magnetic strip by the reader not matching the unique coding assigned to this card as determined by the characterization device of the invention.

The invention claimed is:

1. A method for the individualized characterization of magnetic elements based on ferromagnetic resonance, wherein each of the magnetic elements exhibits properties of ferromagnetic resonance and each of the magnetic elements has a resonance frequency, the method comprising:
    applying in a given area a low-frequency electromagnetic field, wherein the low frequency is between 50-800 Hz;
    simultaneously applying in the given area an electromagnetic wave of a high frequency, between 0.5-20 GHz equal to the resonance frequency of a magnetic element;
    inserting the magnetic element in the given area in order for the magnetic element to absorb the high-frequency electromagnetic wave with a frequency that is the same as that of the low-frequency electromagnetic field, so the high frequency electromagnetic wave is modulated with a frequency equal to the frequency of the low-frequency electromagnetic field;
    receiving a unique and individual modulated wave characteristic of each magnetic element; and
    assigning the unique and individual modulated wave characteristic to each magnetic element,
    wherein the assignment of the unique and individual modulated wave characteristic to each magnetic element includes modifying a modulated wave by using a low frequency hysteresis loop which characterizes the respective magnetic element.

2. The method according to claim 1, wherein the magnetic element is an amorphous magnetic element.

3. The method according to claim 1, wherein the magnetic element is a magnetic microwire.

4. The method according to claim 1, wherein the method is further implemented for identification of magnetic elements, comprising:
    performing an initial characterization on a first magnetic element, thereby obtaining a first unique modulated signal by applying the method of individual characterization;
    applying the method of individual characterization to a second magnetic element and obtaining a second unique modulated wave; and
    comparing the first and second modulated waves and, if they are the same, identifying the second magnetic element as the first magnetic element.

5. A system for the characterization of magnetic elements based on ferromagnetic resonance, wherein each of the magnetic elements exhibits properties of ferromagnetic resonance and each of the magnetic elements has a resonance frequency, the system comprising:
    a means for applying a low-frequency electromagnetic field in a given area, wherein the low frequency is between 50-800 Hz;
    a means for applying a high-frequency electromagnetic wave between 0.5 and 20 GHz, which is equal to the resonance frequency of a magnetic element in the given area;
    a means for controlling simultaneous application of the low-frequency electromagnetic field and the high-frequency electromagnetic wave, such that in response to the introduction of the magnetic element in the given area, the magnetic element absorbs the high-frequency electromagnetic wave with a frequency that is the same as that of the low-frequency electromagnetic field, so the high-frequency electromagnetic wave is modulated with a frequency equal to the frequency of the low-frequency electromagnetic field;

a means for receiving a unique and individual modulated wave characteristic of each magnetic element, and a means for assigning the unique and individual modulated wave characteristic to each magnetic element;

wherein the assignment of the unique and individual modulated wave characteristic to each magnetic element includes modifying a modulated wave by using a low frequency hysteresis loop which characterizes the respective magnetic element.

6. The system according to claim 5, where the means for assignment of the unique and individual modulated wave characteristic of the magnetic element to the magnetic element includes a means for encoding the modulated wave.

7. The system according to claim 5, wherein the magnetic element is an amorphous magnetic element.

8. The system according to claim 5, wherein the magnetic element is a magnetic microwire.

9. The system according to claim 5, wherein the system is implemented for identification of magnetic elements, by:

providing an initial characterization on a first magnetic element, thereby obtaining a first unique modulated signal by applying the system of characterization;

applying the system of characterization to obtain a second unique modulated wave of a second magnetic element; and comparing the first and second modulated waves and, if they are the same, identifying the second magnetic element as the first magnetic element.

* * * * *